(12) United States Patent
Mogensen et al.

(10) Patent No.: US 7,115,112 B2
(45) Date of Patent: Oct. 3, 2006

(54) DEVICE FOR SUBCUTANEOUS ADMINISTRATION OF A MEDICAMENT TO A PATIENT AND TUBING FOR SAME

(75) Inventors: Lasse Wesseltoft Mogensen, Søborg (DK); Magnus Walter Göransson, Göteborg (SE)

(73) Assignee: Unomedical A/S, Lynge (DK)

( * ) Notice: Subject to any disclaimer, the term of this patent is extended or adjusted under 35 U.S.C. 154(b) by 45 days.

(21) Appl. No.: 10/517,024

(22) PCT Filed: Sep. 1, 2003

(86) PCT No.: PCT/DK03/00568

§ 371 (c)(1),
(2), (4) Date: Dec. 6, 2004

(87) PCT Pub. No.: WO2004/020035

PCT Pub. Date: Mar. 11, 2004

(65) Prior Publication Data

US 2006/0058733 A1 Mar. 16, 2006

(30) Foreign Application Priority Data

Sep. 2, 2002 (DK) .............................. 2002 01285

(51) Int. Cl.
*A61M 5/32* (2006.01)

(52) U.S. Cl. ....................................... 604/177; 604/523
(58) Field of Classification Search ................ 604/177, 604/264, 523, 525, 530, 535, 539
See application file for complete search history.

(56) References Cited

U.S. PATENT DOCUMENTS 643,544 A 2/1900 Simmons (Continued)

FOREIGN PATENT DOCUMENTS

DE 893 296 12/1953

(Continued)

OTHER PUBLICATIONS

Copy of International Search Report, dated Jan. 21, 2004.

*Primary Examiner*—Nicholas Lucchesi
*Assistant Examiner*—Laura A. Bouchelle
(74) *Attorney, Agent, or Firm*—Brinks Hofer Gilson & Lione

(57) ABSTRACT

The invention relates to a device for subcutaneous administration of a medicament to a patient, comprising a cannula housing (1) with an interior chamber; a cannula (2) connected to the cannula housing (1) and being in flow communication with the interior chamber; a tubing (4) manufactured from a flexible material and having a first end (4'), coupled to the cannula housing (1) in such a manner that the tubing (4) is in flow communication with the interior chamber; and wherein the tubing (4), at the other end, carries a source coupling (5), by which the tubing can be coupled to a source for said medicament. The invention is characterised in that, at least over a section of its length, the tubing comprises a longitudinally extending, external groove (12) and a longitudinally extending, external protrusion (11) arranged diametrically opposite the groove (12) and complementary with said groove (12); and that, using the flexibility of its material, the groove (12) is configured for being able to receive and secure the protrusion (11) in a releasable manner in a configuration of the tubing (4), in which the tubing (4) is folded (9) for forming parallel courses of tubing (14, 24, 34). The invention also relates to a tubing configured for use in said device.

8 Claims, 4 Drawing Sheets

U.S. PATENT DOCUMENTS

| | | |
|---|---|---|
| 1,838,825 A | 12/1931 | Goldstein |
| 1,991,103 A | 2/1935 | King |
| 2,047,010 A | 7/1936 | Dickinson |
| 2,295,849 A | 9/1942 | Kayden |
| 2,319,731 A | 5/1943 | Garrett |
| 2,533,731 A | 12/1950 | Gomberg |
| 2,630,803 A | 3/1953 | Baran |
| 2,690,529 A | 9/1954 | Lindblad |
| 2,730,099 A | 1/1956 | Sullivan |
| 2,839,060 A | 6/1958 | Ormo |
| 2,936,141 A | 5/1960 | Rapala |
| 2,952,420 A | 9/1960 | Von Hoorn |
| 3,055,361 A | 9/1962 | Ballard |
| 3,074,541 A | 1/1963 | Roehr |
| 3,107,785 A | 10/1963 | Roehr |
| 3,154,080 A | 10/1964 | Rowan et al. |
| 3,317,166 A | 5/1967 | Janssen |
| 3,545,286 A | 12/1970 | Stenstrom |
| 3,610,240 A | 10/1971 | Harautuneian |
| 3,648,999 A | 3/1972 | Bauer |
| 3,783,996 A | 1/1974 | Gerard et al. |
| 3,814,097 A | 6/1974 | Ganderton et al. |
| 3,831,729 A | 8/1974 | Howard |
| 3,840,011 A | 10/1974 | Wright |
| 3,865,236 A | 2/1975 | Rycroft |
| 3,942,528 A | 3/1976 | Loeser |
| 4,014,328 A | 3/1977 | Cluff et al. |
| 4,146,113 A | 3/1979 | Gavel |
| 4,150,798 A | 4/1979 | Aragon |
| 4,188,950 A | 2/1980 | Wardlaw |
| 4,227,528 A | 10/1980 | Wardlaw |
| 4,267,836 A | 5/1981 | Whitney et al. |
| 4,306,705 A | 12/1981 | Svenson |
| D267,199 S | 12/1982 | Koenig |
| 4,365,630 A | 12/1982 | McFarlane |
| 4,400,861 A | 8/1983 | Parker |
| 4,406,042 A | 9/1983 | McPhee |
| 4,458,344 A | 7/1984 | Coogler |
| 4,472,024 A | 9/1984 | Konomura et al. |
| 4,517,971 A | 5/1985 | Sorbonned |
| 4,530,695 A | 7/1985 | Phillips et al. |
| 4,531,686 A | 7/1985 | Shaw |
| 4,576,846 A | 3/1986 | Noel |
| 4,606,735 A | 8/1986 | Wilder et al. |
| 4,616,790 A | 10/1986 | Beltran |
| 4,619,349 A | 10/1986 | Braun |
| 4,635,683 A | 1/1987 | Nielsen |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,734,092 A | 3/1988 | Millerd |
| 4,755,173 A | 7/1988 | Konopka et al. |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,878,897 A | 11/1989 | Katzin |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,045 A | 2/1991 | Ranford |
| 5,011,475 A | 4/1991 | Olsen |
| 5,024,662 A | 6/1991 | Menes et al. |
| 5,077,872 A | 1/1992 | Guthammar |
| 5,083,757 A | 1/1992 | Barsky |
| 5,098,389 A | 3/1992 | Cappucci |
| 5,112,313 A | 5/1992 | Sallee |
| 5,116,319 A | 5/1992 | Van den Haak |
| 5,116,324 A | 5/1992 | Brierley et al. |
| 5,116,325 A | 5/1992 | Paterson |
| 5,121,751 A | 6/1992 | Panalletta |
| 5,134,593 A | 7/1992 | Logan et al. |
| 5,134,594 A | 7/1992 | Woo |
| 5,141,496 A | 8/1992 | Dalto et al. |
| 5,147,319 A | 9/1992 | Ishikawa et al. |
| 5,147,375 A | 9/1992 | Sullivan et al. |
| 5,161,681 A | 11/1992 | Kemp et al. |
| 5,163,915 A | 11/1992 | Holleron |
| 5,176,662 A | 1/1993 | Bartholomew et al. |
| 5,188,314 A | 2/1993 | Peters |
| 5,188,611 A | 2/1993 | Orgain |
| RE34,223 E | 4/1993 | Bonaldo |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,152 A | 10/1993 | Marks |
| 5,257,980 A | 11/1993 | Van Antwerp et al. |
| 5,265,822 A | 11/1993 | Shober, Jr. et al. |
| 5,269,799 A | 12/1993 | Daniel |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A * | 5/1994 | Scott et al. ............... 248/68.1 |
| 5,324,302 A | 6/1994 | Crouse |
| 5,342,319 A | 8/1994 | Watson et al. |
| 5,342,324 A | 8/1994 | Tucker |
| 5,343,637 A | 9/1994 | Schindler |
| 5,350,392 A | 9/1994 | Purcell et al. |
| 5,354,280 A | 10/1994 | Haber et al. |
| 5,366,469 A | 11/1994 | Steg et al. |
| 5,372,592 A * | 12/1994 | Gambale .................... 604/523 |
| 5,376,082 A | 12/1994 | Phelps |
| 5,384,174 A | 1/1995 | Ward et al. |
| 5,387,197 A | 2/1995 | Smith et al. |
| 5,388,931 A | 2/1995 | Carlson |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,433,307 A | 7/1995 | Jeppe |
| D362,718 S | 9/1995 | Deily et al. |
| 5,449,349 A | 9/1995 | Sallee et al. |
| 5,487,506 A | 1/1996 | Drummond et al. |
| 5,490,841 A | 2/1996 | Landis |
| 5,492,313 A | 2/1996 | Pan et al. |
| 5,505,709 A | 4/1996 | Funderburk et al. |
| 5,507,730 A | 4/1996 | Haber et al. |
| 5,519,167 A | 5/1996 | Kunimoto et al. |
| 5,520,654 A | 5/1996 | Wahlberg |
| 5,522,803 A | 6/1996 | Teissen-Simony |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,554,130 A | 9/1996 | McDonald et al. |
| 5,558,650 A | 9/1996 | McPhee |
| 5,562,636 A | 10/1996 | Utterberg |
| 5,584,813 A | 12/1996 | Livingston et al. |
| 5,591,188 A | 1/1997 | Waisman |

| | | | | | |
|---|---|---|---|---|---|
| 5,599,309 | A | 2/1997 | Marshall et al. | 6,595,962 B1 | 7/2003 Perthu |
| 5,599,315 | A | 2/1997 | McPhee | 6,607,509 B1 | 8/2003 Bobroff et al. |
| 5,599,318 | A | 2/1997 | Sweeney et al. | 6,607,511 B1 | 8/2003 Halseth et al. |
| 5,643,214 | A | 7/1997 | Marshall | 6,629,949 B1 | 10/2003 Douglas |
| 5,643,220 | A | 7/1997 | Cosme | 6,685,674 B1 | 2/2004 Douglas et al. |
| 5,662,617 | A | 9/1997 | Odell et al. | 6,702,779 B1 | 3/2004 Connelly et al. |
| 5,665,071 | A | 9/1997 | Wyrick | 6,726,649 B1 | 4/2004 Swenson et al. |
| 5,665,075 | A | 9/1997 | Gyure et al. | 6,736,797 B1 | 5/2004 Larsen et al. |
| 5,681,323 | A | 10/1997 | Arick | 6,749,589 B1 | 6/2004 Douglas et al. |
| 5,695,476 | A | 12/1997 | Harris | 6,790,199 B1 | 9/2004 Gianakos |
| 5,704,920 | A | 1/1998 | Gyure | 6,811,545 B1 | 11/2004 Vaillancourt |
| 5,709,516 | A | 1/1998 | Peterson et al. | 6,814,720 B1 | 11/2004 Olsen et al. |
| 5,714,225 | A | 2/1998 | Hansen et al. | 6,824,530 B1 | 11/2004 Wagner et al. |
| 5,741,288 | A | 4/1998 | Rife | 6,824,531 B1 | 11/2004 Zecha, Jr. et al. |
| 5,752,923 | A | 5/1998 | Terwilliger | 6,830,562 B1 | 12/2004 Mogensen et al. |
| 5,810,835 | A | 9/1998 | Ryan et al. | 6,880,701 B1 | 4/2005 Bergeron et al. |
| 5,820,598 | A | 10/1998 | Gazza et al. | 6,916,017 B1 | 7/2005 Noe |
| D402,538 | S | 12/1998 | Wagter et al. | 6,923,791 B1 | 8/2005 Douglas |
| 5,851,197 | A | 12/1998 | Marano et al. | 6,926,694 B1 | 8/2005 Marano-Ford et al. |
| 5,865,806 | A | 2/1999 | Howell | 6,949,084 B1 | 9/2005 Marggi et al. |
| 5,873,540 | A | 2/1999 | Hardin | 2001/0004970 A1 | 6/2001 Hollister et al. |
| 5,899,886 | A | 5/1999 | Cosme | 2001/0016714 A1 | 8/2001 Bell et al. |
| 5,915,640 | A | 6/1999 | Wagter et al. | 2001/0021827 A1 | 9/2001 Ferguson et al. |
| 5,925,032 | A | 7/1999 | Clements | 2001/0039401 A1 | 11/2001 Ferguson et al. |
| 5,947,935 | A | 9/1999 | Rinehart et al. | 2001/0041875 A1 | 11/2001 Higuchi et al. |
| 5,951,523 | A | 9/1999 | Osterlind et al. | 2002/0022855 A1 | 2/2002 Bobroff et al. |
| 5,954,643 | A | 9/1999 | VanAntwerp et al. | 2002/0068904 A1 | 6/2002 Pluth et al. |
| 5,957,892 | A | 9/1999 | Thorne | 2002/0072720 A1 | 6/2002 Hague et al. |
| 5,968,011 | A | 10/1999 | Larsen et al. | 2002/0107489 A1 | 8/2002 Lee |
| 5,975,120 | A | 11/1999 | Novosel | 2002/0111581 A1 | 8/2002 Sasso |
| 5,980,488 | A | 11/1999 | Thorne | 2002/0145073 A1 | 10/2002 Swanson |
| 5,980,506 | A | 11/1999 | Mathiasen | 2002/0156427 A1 | 10/2002 Suzuki et al. |
| 5,984,224 | A | 11/1999 | Yang | 2002/0161332 A1 | 10/2002 Ramey |
| 5,984,897 | A | 11/1999 | Peterson et al. | 2002/0169419 A1 | 11/2002 Steg |
| 5,992,787 | A | 11/1999 | Burke | 2002/0173748 A1 | 11/2002 McConnell et al. |
| 6,017,328 | A | 1/2000 | Fischell et al. | 2002/0183688 A1 | 12/2002 Lastovich et al. |
| 6,039,629 | A | 3/2000 | Mitchell | 2002/0189688 A1 | 12/2002 Roorda |
| 6,042,570 | A | 3/2000 | Bell et al. | 2002/0193737 A1 | 12/2002 Popovsky |
| 6,045,533 | A | 4/2000 | Kriesel et al. | 2002/0193744 A1 | 12/2002 Alesi et al. |
| 6,050,976 | A | 4/2000 | Thorne et al. | 2003/0069548 A1 | 4/2003 Connelly et al. |
| 6,056,718 | A | 5/2000 | Funderburk et al. | 2003/0109829 A1 | 6/2003 Mogensen et al. |
| 6,074,371 | A | 6/2000 | Fischell | 2003/0125669 A1 | 7/2003 Safabash et al. |
| 6,086,008 | A | 7/2000 | Gray et al. | 2003/0125678 A1 | 7/2003 Swenson et al. |
| 6,086,575 | A | 7/2000 | Mejslov | 2003/0130619 A1 | 7/2003 Safabash et al. |
| 6,090,068 | A | 7/2000 | Chanut | 2003/0139704 A1 | 7/2003 Lin |
| 6,093,172 | A | 7/2000 | Funderburk et al. | 2003/0158520 A1 | 8/2003 Safabash et al. |
| 6,093,179 | A | 7/2000 | O'Hara et al. | 2003/0176843 A1 | 9/2003 Wilkinson |
| 6,099,503 | A | 8/2000 | Stardella | 2003/0181863 A1 | 9/2003 Davis et al. |
| 6,105,218 | A | 8/2000 | Reekie | 2003/0181868 A1 | 9/2003 Swenson |
| 6,120,482 | A | 9/2000 | Szabo | 2003/0181873 A1 | 9/2003 Swenson |
| 6,123,690 | A | 9/2000 | Mejslov | 2003/0187394 A1 | 10/2003 Wilkinson et al. |
| 6,132,755 | A | 10/2000 | Eicher et al. | 2003/0187395 A1 | 10/2003 Wilkinson et al. |
| 6,183,464 | B1 | 2/2001 | Sharp et al. | 2003/0199823 A1 | 10/2003 Bobroff et al. |
| 6,193,694 | B1 | 2/2001 | Bell et al. | 2003/0216686 A1 | 11/2003 Lynch et al. |
| 6,219,574 | B1 | 4/2001 | Cormier et al. | 2003/0225373 A1 | 12/2003 Bobroff et al. |
| 6,221,058 | B1 | 4/2001 | Kao et al. | 2003/0225374 A1 | 12/2003 Mathiasen |
| 6,248,093 | B1 | 6/2001 | Moberg | 2003/0229308 A1 | 12/2003 Tsals et al. |
| 6,293,925 | B1 | 9/2001 | Safabash et al. | 2003/0229316 A1 | 12/2003 Hwang et al. |
| 6,302,866 | B1 | 10/2001 | Marggi | 2004/0002682 A1 | 1/2004 Kovelman et al. |
| 6,322,535 | B1 | 11/2001 | Hitchins et al. | 2004/0006316 A1 | 1/2004 Patton |
| 6,322,808 | B1 | 11/2001 | Trautman et al. | 2004/0026840 A1 | 2/2004 Eckel et al. |
| 6,334,856 | B1 | 1/2002 | Allen et al. | 2004/0044306 A1 | 3/2004 Lynch et al. |
| 6,355,021 | B1 | 3/2002 | Nielsen et al. | 2004/0049159 A1 | 3/2004 Barrus et al. |
| 6,379,335 | B1 | 4/2002 | Rigon et al. | 2004/0068231 A1 | 4/2004 Blondeau |
| D456,692 | S | 5/2002 | Epstein | 2004/0087913 A1 | 5/2004 Rogers et al. |
| 6,387,076 | B1 | 5/2002 | Landuyt | 2004/0111068 A1 | 6/2004 Swenson |
| 6,488,663 | B1 | 12/2002 | Steg | 2004/0112781 A1 | 6/2004 Hofverberg et al. |
| 6,517,517 | B1 | 2/2003 | Farrugia et al. | 2004/0116865 A1 | 6/2004 Bengtsson |
| 6,520,938 | B1 | 2/2003 | Funderburk et al. | 2004/0138620 A1 | 7/2004 Douglas et al. |
| D472,316 | S | 3/2003 | Douglas et al. | 2004/0143216 A1 | 7/2004 Douglas et al. |
| D472,630 | S | 4/2003 | Douglas et al. | 2004/0143218 A1 | 7/2004 Das |
| 6,572,586 | B1 | 6/2003 | Wojcik | 2004/0158202 A1 | 8/2004 Jensen |
| 6,579,267 | B1 | 6/2003 | Lynch et al. | 2004/0158207 A1 | 8/2004 Hunn et al. |

| | | | | | | |
|---|---|---|---|---|---|---|
| 2004/0162518 | A1 | 8/2004 | Connelly et al. | EP | 0 956 879 A1 | 7/2004 |
| 2004/0171989 | A1 | 9/2004 | Horner et al. | FR | 576 849 | 8/1924 |
| 2004/0178098 | A1 | 9/2004 | Swenson et al. | FR | 576849 | 8/1924 |
| 2004/0186446 | A1 | 9/2004 | Ohshima | FR | 2 611 013 | 8/1988 |
| 2004/0199123 | A1 | 10/2004 | Nielsen | FR | 2725902 | 10/1994 |
| 2004/0204687 | A1 | 10/2004 | Mogensen et al. | FR | 2 733 915 | 11/1996 |
| 2004/0204690 | A1 | 10/2004 | Yashiro et al. | FR | 2733915 A1 | 11/1996 |
| 2004/0220528 | A1 | 11/2004 | Garcia, Jr. | FR | 2 781 617 A1 | 1/2000 |
| 2004/0238392 | A1 | 12/2004 | Peterson et al. | FR | 2781617 A1 | 1/2000 |
| 2004/0243065 | A1 | 12/2004 | McConnell et al. | GB | 478803 | 1/1938 |
| 2004/0254433 | A1 | 12/2004 | Bandis et al. | GB | 591730 | 3/1946 |
| 2004/0260235 | A1 | 12/2004 | Douglas | GB | 906574 | 9/1962 |
| 2004/0260250 | A1 | 12/2004 | Harris et al. | GB | 1 268 575 | 3/1972 |
| 2005/0035014 | A1 | 2/2005 | Cane | GB | 1 403 034 | 8/1975 |
| 2005/0101932 | A1 | 5/2005 | Cote et al. | GB | 2 224 808 A | 5/1990 |
| 2005/0101933 | A1 | 5/2005 | Marrs et al. | GB | 2 270 552 A | 3/1994 |
| 2005/0107746 | A1 | 5/2005 | Fangrow, Jr. | JP | 5326062 A | 12/1993 |
| 2005/0113761 | A1 | 5/2005 | Faust et al. | JP | 05326062 A | 12/1993 |
| 2005/0119637 | A1 | 6/2005 | Lundgren et al. | JP | 7051251 | 11/1995 |
| 2005/0124936 | A1 | 6/2005 | Mogensen et al. | JP | 9217584 A | 8/1997 |
| 2005/0159709 | A1 | 7/2005 | Wilkinson | JP | 2000-59877 A | 2/2000 |
| 2005/0215979 | A1 | 9/2005 | Konerup et al. | JP | 3140740 | 2/2000 |
| 2005/0277892 | A1 | 12/2005 | Chen | JP | 2000059877 A | 2/2000 |
| 2005/0283114 | A1 | 12/2005 | Bresina et al. | JP | 3140740 B2 | 3/2001 |
| | | | | JP | 2002-028246 | 1/2002 |

FOREIGN PATENT DOCUMENTS

| | | | | | |
|---|---|---|---|---|---|
| DE | 1 053 541 | 3/1959 | NL | 1017427 C | 11/2002 |
| DE | DT 26 20 009 A1 | 12/1977 | WO | WO 87/06474 | 11/1987 |
| DE | 28 03 509 | 8/1979 | WO | WO 93/03787 | 3/1993 |
| DE | 298 18 311 U1 | 11/1999 | WO | WO 93/05840 | 4/1993 |
| DE | 101 06 074 A1 | 9/2000 | WO | WO 94/20160 | 9/1994 |
| DE | 299 21 406 U1 | 11/2002 | WO | WO 95/28327 A | 10/1995 |
| DK | DT 26 20 009 A1 | 12/1977 | WO | WO 96/35472 | 11/1996 |
| DK | 37 22 893 C1 | 6/1988 | WO | WO 98/09065 | 3/1998 |
| DK | 38 23 447 | 2/1996 | WO | WO 98/58693 | 12/1998 |
| DK | 196 10 692 A1 | 9/1997 | WO | WO 99/07435 | 2/1999 |
| DK | 198 47 143 A1 | 1/2000 | WO | WO 99/33504 | 7/1999 |
| DK | 100 49 001 A1 | 4/2002 | WO | WO 99/36009 | 7/1999 |
| EP | 0 188 014 B1 | 10/1985 | WO | WO 99/56802 | 11/1999 |
| EP | 0 298 521 B1 | 9/1990 | WO | WO 99/61815 | 12/1999 |
| EP | 0 184 231 B1 | 1/1992 | WO | WO 00/02614 | 1/2000 |
| EP | 0 475 857 | 3/1992 | WO | WO 00/03757 | 1/2000 |
| EP | 0 544 837 B1 | 6/1993 | WO | WO 00/44324 A1 | 8/2000 |
| EP | 0 651 662 B1 | 5/1995 | WO | WO 01/04507 A1 | 1/2001 |
| EP | 0 714 631 B1 | 6/1996 | WO | WO 01/30419 A2 | 5/2001 |
| EP | 0 747 006 A1 | 12/1996 | WO | WO 01/68180 | 9/2001 |
| EP | 0 688 232 B1 | 12/1998 | WO | WO 01/81785 A1 | 11/2001 |
| EP | 0 884 108 A1 | 12/1998 | WO | WO 01/93926 A2 | 12/2001 |
| EP | 0 916 361 A1 | 5/1999 | WO | WO 02/46080 | 6/2002 |
| EP | 0 931 560 A1 | 7/1999 | WO | WO 02/066854 A1 | 8/2002 |
| EP | 0 956 879 A1 | 11/1999 | WO | WO 02/094352 | 11/2002 |
| EP | 1 045 145 A1 | 10/2000 | WO | WO 02/100457 | 12/2002 |
| EP | 1 060 757 A1 | 12/2000 | WO | WO 02/068014 | 1/2003 |
| EP | 1 086 718 A | 3/2001 | WO | WO 03/015860 A1 | 2/2003 |
| EP | 1 125 593 A1 | 8/2001 | WO | WO 03/026728 | 4/2003 |
| EP | 1 167 765 A2 | 1/2002 | WO | WO 04/030726 A | 4/2004 |
| EP | 0 775 501 | 6/2002 | WO | WO 04/087240 | 10/2004 |
| EP | 0 894 216 B1 | 7/2003 | WO | WO 05/004973 | 1/2005 |

* cited by examiner

DEVICE FOR SUBCUTANEOUS ADMINISTRATION OF A MEDICAMENT TO A PATIENT AND TUBING FOR SAME

This application is a continuation of International Application No. PCT/DK2003/000568, filed Sep. 1, 2003, which is a continuation of Danish Application No. PA 2002 01285, filed Sep. 2, 2002, these references are incorporated herein in their entirety.

The present invention relates to a device for subcutaneous administration of a medicament to a patient, comprising a cannula housing with an interior chamber, a cannula connected to said cannula housing and in flow communication with the interior chamber, and a tubing manufactured from a flexible material and having a first end and a second end, wherein the tubing is, at its first end, coupled to the cannula housing such that the tubing is in flow communication with the interior chamber, and wherein, at its second end, the tubing carries a source coupling by which the tubing can be coupled to a source for said medicament.

U.S. Pat. No. 5,522,803, being now as a reference deemed to constitute a part of the present text, shows in FIGS. 1 and 2 a cannula housing to be adhered to the skin of the patient, so as to enable continuous administration of a drug to the patient via a plastics needle introduced into the skin of the patient. At its one end a tubing features a source coupling by which the tubing can be coupled to a source, such as a pump, thereby enabling the drug to be fed to the cannula housing through the tubing. At its other end, the tubing has a coupling that is releasably secured to the cannula housing, whereby the tubing can be released from the cannula housing, eg when the patient is in the bath.

In some situations, eg when the patient is asleep it is necessary to have a relatively long distance between the cannula housing and the source of the drug to enable the source of drug to sit on a table next to the patient. Thus there is a need for a comparatively long tubing, eg a tubing having a length of about 1.1 m. Conversely, a short tubing is typically desired when the patient is up and about, ie when the source of drug is carried by the patient, eg in a pocket in his clothes. To overcome this problem, it is an option to change tubing as day turns into night. This, however, may lead to waste of the usually very expensive medicament located in the long tubing.

It is previously been attempted to solve this problem by providing the source of drug with a winder mechanism for the tubing, see international patent application No. WO 96/35472. The winder mechanism described therein, however, cannot be manufactured at low costs and there is a risk of the winder mechanism getting stuck.

It is the object of the present invention to provide a device for subcutaneous administration of a drug to a patient that can be be manufactured at low costs and that enables variations in the distance between the source of drug and the cannula housing without using a complex mechanism.

This is accomplished in the tubing having, at least in a section of its length, a longitudinally extending external groove and a longitudinally extending external protrusion complementary therewith and arranged diametrically opposite the groove, and wherein the groove is configured for using the flexibility of the material for receiving and securing the protrusion in a releasable manner in a configuration of the tubing in which the tubing is folded for forming parallel courses of the tubing.

Alternatively it is an option to provide, within the scope of the invention, a holder device for securing the tubing in a configuration in which the tubing is folded for forming at least two parallel courses of tubing, the holder device comprising a plate with at least two parallel grooves configured for being able to receive and secure the tubing in a releasable manner in said configuration.

The invention also relates to a flexible extruded tubing suitable for establishing a configuration of the tubing in which the tubing is folded for forming parallel, adjacently arranged courses of tubing, preferably for use in connection with a device for subcutaneous supply of a medicament, wherein the tubing has, at least over a section of its length, a longitudinally extending, external groove and a longitudinally extending, external protrusion complementary therewith and arranged diametrically opposite the groove, said groove being configured for utilising the flexibility of the tubing for being able to receive and secure the protrusion in a releasable manner in said configuration of the tubing.

In the present context, the term "parallel courses of tubing" is intended to designate one or two length(s) of the tubing that has/have—apart from the folding area—courses that are mutually parallel and situated closely to each other. It will be understood that the user may freely choose to provide either a relatively large number of folds with a correspondingly large number of short courses of tubing or few folds with few relatively long courses of tubing. Also, the term "folded" is intended to designate a state in which the tubing continues to be able to convey medicament from the one end of the tubing to the other.

The invention will now be explained in further detail with reference to the drawing.

Figure 1:
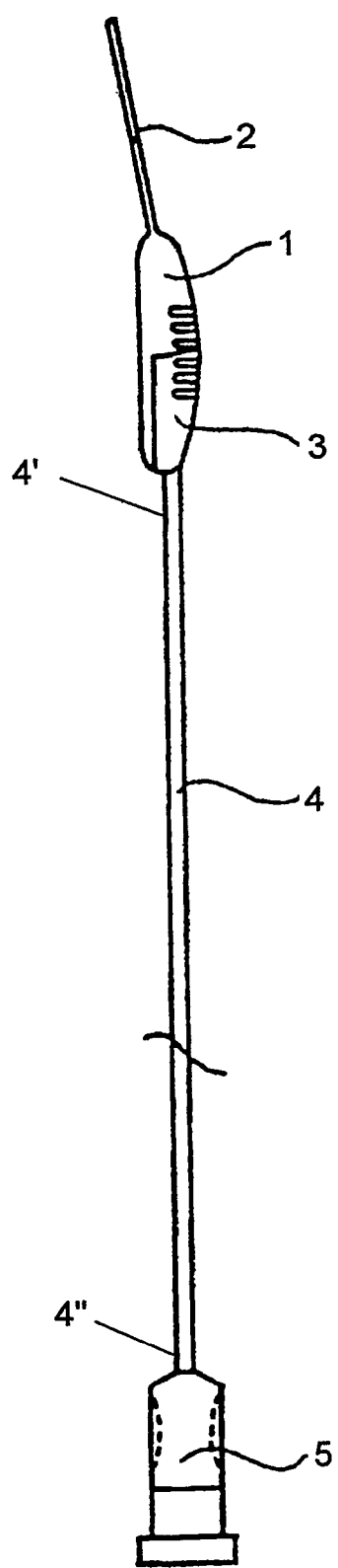
FIG. 1 is a schematic view of a number of the elements used for subcutaneous administration of a medicament to a patient.
Figure 2:
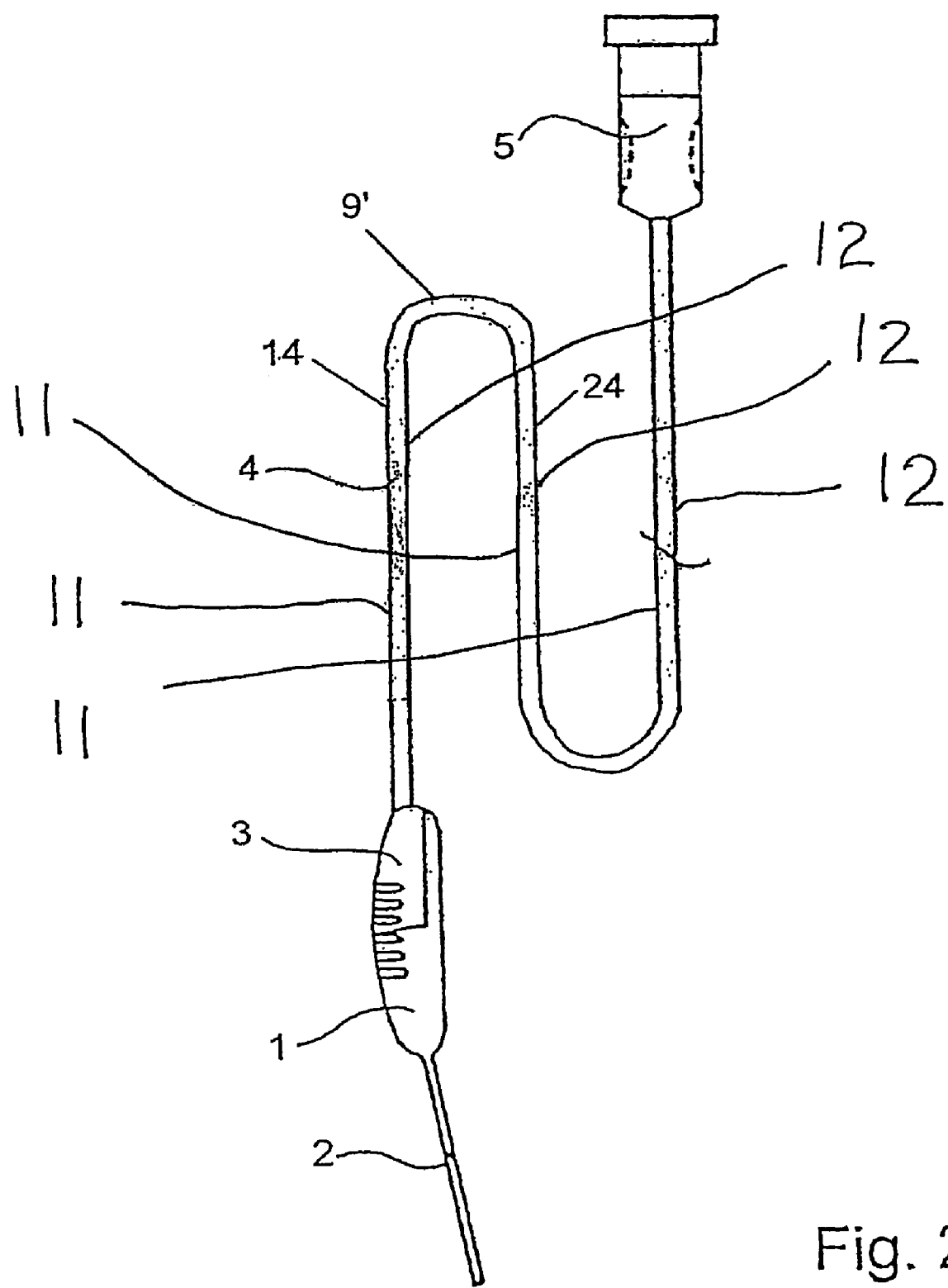
FIG. 2 shows the device shown in FIG. 1, wherein the tubing has been caused to assume a folded configuration with three parallel courses of tubing.

FIG. 3 schematically shows an embodiment in which the tubing shown in FIG. 2 has complementary grooves and protrusions and wherein the courses of the tubings are interconnected; and FIG. 4 shows an alternative embodiment, wherein the tubing shown in FIG. 1 has an ordinary, circular cross section and is mounted on a plate for securing the tubing in a folded configuration.

FIG. 1 shows a part of a flexible tubing 4 having a first end 4' and a second end 4". At its first end 4' the tubing 4 is provided with a coupling 3 configured for being, in a releasable manner, able to be secured to a cannula housing 1. The cannula housing 1 has an interior chamber that communicates with the tubing 4 and with a cannula 2 that protrudes from the cannula housing 1, said cannula preferably being flexible and of plastics and intended for being introduced through the surface of the skin of a patient by means of a not shown introduction needle. The interior chamber is not shown, but its configuration may like the one shown in U.S. Pat. No. 5,522,803.

A source coupling 5 secured to the second end 4" of the tubing 4 makes it possible to releasably couple the tubing to a source for a drug. The term 'source' in this context is intended to designate a receptacle for the drug, since, between the receptacle and the coupling 5, a pump is preferably introduced that supplies the drug to the patient via the tubing 4 in a predetermined dosage. The source coupling 5 is configured for being able to co-operate with a complementary coupling on said drug receptacle or on a tubing connected to the receptacle or pump. Preferably the tubing is made of a plastics material and has such properties that, to a wide extent, the tubing 4 is able to prevent a local occlusion of the flow of the drug if the tubing 4 is folded sharply.

FIG. 2 shows a configuration in which the tubing shown in FIG. 1 is bent twice, whereby three parallel courses for the tubing is provided, the two of which are indicated by numerals 14 and 24.

Figure 3A:
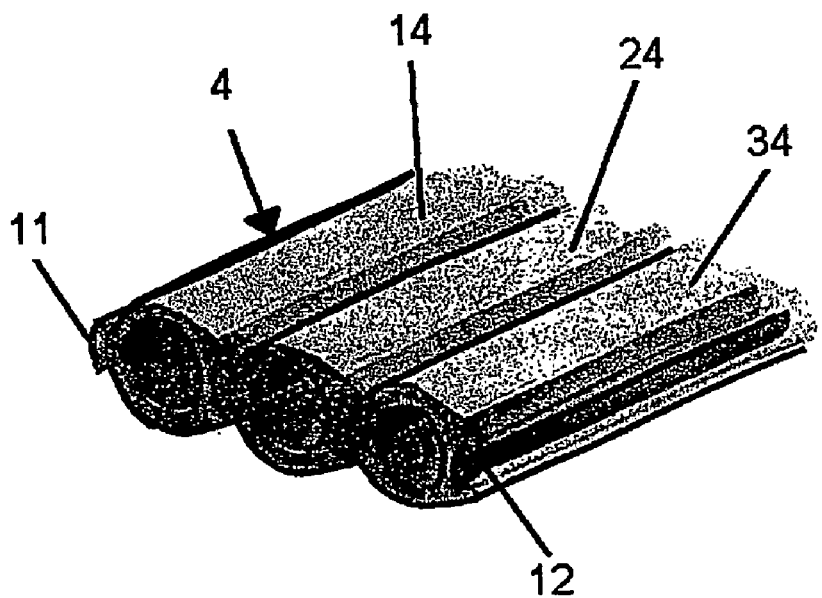
Figure 3B:
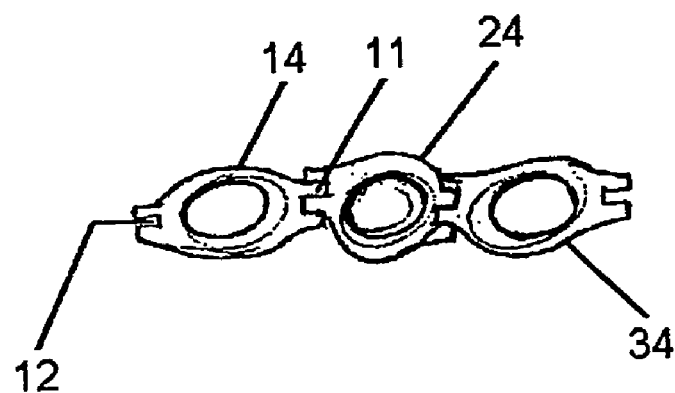

According to a first embodiment of the invention as shown in FIGS. 3a and 3b, the tubing shown in FIG. 2 is provided with a longitudinally extending protrusion 11 and a longitudinally extending groove 12. The protrusion 11 and the groove 12 preferably extend from the first end 4' of the tubing 4 to the second end 4" of the tubing 4, the tubing 4 being preferably manufactured by extrusion. The groove 12 is complementary with the protrusion 11, by which is to be understood that the protrusion 11 can be received in the groove 12 and secured in the groove in a releasable manner by using the flexibility/elasticity of the material. This is preferably acquired as shown in FIG. 3a by the protrusion being dovetail-shaped and by the mouthing of the groove 12 expanding slightly when the protrusion 11 is introduced, following which the mouthing of the groove 12 again contracts slightly, thereby securing that the protrusion 11 is secured in the groove 12. As shown in FIG. 3b, the groove 12 and the protrusion 11 can be configured for providing a friction force that secures the protrusion 11.

Figure 4A:
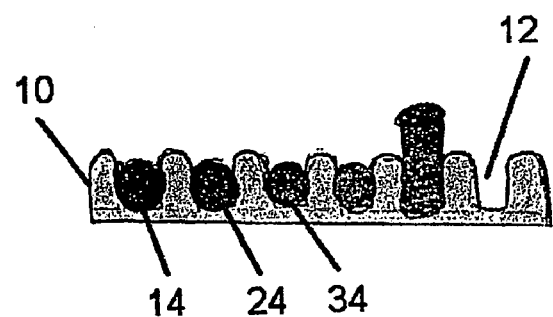
Figure 4B:
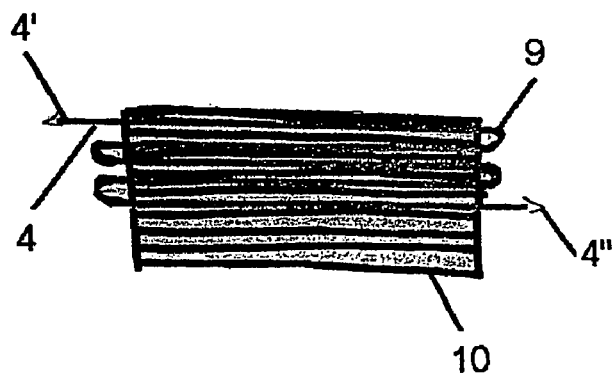
Figure 4C:
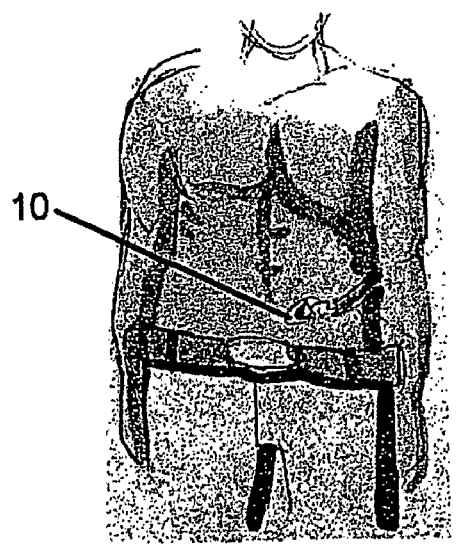

According to an alternative embodiment of the invention, as shown in FIG. 4a, a holder device 10 can be mounted in the form of a sheet element on the tubing 4 for securing the tubing 4 in a folded state, whereby a controlled configuration is provided with eg five courses of tubing 14, 24, 34 extending in parallel with each other. The tubing 4 has a usual round cross section, and the holder device 10 has longitudinally extending, parallel grooves 12 of width corresponding approximately to the diameter of the tubing 4, such that the tubing can be received and secured in the groove 12 following introduction into the groove 12. During this introduction the elasticity of the material can optionally be useful, as the groove 12 may expand slightly. The holder device 10 with the tubing 4 is shown in FIG. 4b, seen from above, and the holder device may comprise means, such as a belt, by which the holder device 10 can be secured to the patient, as shown in FIG. 4c.

The invention claimed is:

1. A device for subcutaneous administration of a medicament to a patient, comprising:
    a cannula housing (1) with an interior chamber;
    a cannula (2) connected to the cannula housing (1) and being in flow communication with the interior chamber;
    a tubing (4) manufactured from a flexible material and having a first end (4') and a second end (4"), wherein the tubing (4) is, at the first end (4'), coupled to the cannula housing (1) in such a manner that the tubing (4) is in flow communication with the interior chamber; and wherein the tubing (4), at the other end, carries a source coupling (5), by which the tubing (4) can be coupled to a source for said medicament,
    characterised in
        that, at least over a part of its length, the tubing comprises a longitudinally extending, external groove (12) and a longitudinally extending, external protrusion (11) complementary with said groove (12); and
        that, using the flexibility of its material, the groove (12) is configured for being able to receive and secure the protrusion (11) in a releasable manner in a configuration of the tubing (4), in which the tubing (4) is folded (9) for forming parallel courses of tubing (14, 24, 34).

2. A device according claim 1, said external protrusion (11) being arranged diametrically opposite the groove (12).

3. A device according to claim 1, characterised in that the tubing (4) with the groove (12) and the protrusion (11) is manufactured by extrusion of a plastics material.

4. A device according to the preceding claim, characterised in that the protrusion (11) is dovetail-shaped.

5. A device for subcutaneous administration of a medicament to a patient, comprising:
    a cannula housing (1) with an interior chamber;
    a cannula (2) connected to the cannula housing (1) and being in flow communication with the interior chamber;
    a tubing (4) manufactured from a flexible material and having a first end (4') and a second end (4"), wherein the tubing (4) is, at the first end (4'), coupled to the cannula housing (1) in such a manner that the tubing (4) is in flow communication with the interior chamber; and wherein the tubing (4), at the other end, carries a source coupling (5), by which the tubing (4) can be coupled to a source for said medicament,
    characterised in
        a holder device (10) for securing the tubing (4) in a configuration in which the tubing (4) is folded for forming at least two parallel courses of tubing (14, 24, 34) with said first end (4') and said second end (4") extending therefrom, and
        said holder device (10) comprising a plate with at least two parallel grooves (12) configured for being able to receive and secure said courses of tubing (14, 24, 34) in a releasable manner in said configuration of the tubing (4).

6. A device according to claim 5, wherein the tubing (4) is folded for forming at least three essentially parallel courses (14, 24, 34) of tubing.

7. An extruded flexible tubing, in particular for use in connection with a device according to claim 1, wherein the tubing (4) is, at least over a part of its length, provided with a longitudinally extending, external groove (12) and a longitudinally extended protrusion (11) complementary therewith; and
    wherein, using the flexibility of the tubing (4), the groove (12) is configured for being able to receive and secure the protrusion (11) in a releasable manner in a configuration of the tubing (4), in which the tubing (4) is folded for forming parallel courses (14, 24, 34) of tubing.

8. The device of claim 1 wherein the tubing is folded for forming at least three essentially parallel courses of tubing.

* * * * *